United States Patent [19]

Tsubokura et al.

[11] Patent Number: 5,607,839

[45] Date of Patent: Mar. 4, 1997

[54] BACTERIA BELONGING TO NEW GENUS PROCESS FOR PRODUCTION OF CAROTENOIDS USING SAME

[75] Inventors: Akira Tsubokura, Kawasaki; Hisashi Yoneda, Yokohama; Mikihiro Takaki, Kawasaki; Takashi Kiyota, Yokohama, all of Japan

[73] Assignee: Nippon Oil Company, Ltd., Tokyo, Japan

[21] Appl. No.: 276,943

[22] Filed: Jul. 19, 1994

[30] Foreign Application Priority Data

Jul. 22, 1993 [JP] Japan ................................. 5-181615

[51] Int. Cl.⁶ ........................................... C12P 23/00
[52] U.S. Cl. ................................... 435/67; 435/252.1
[58] Field of Search .............................. 435/67, 252.1

[56] References Cited

U.S. PATENT DOCUMENTS

| | | | |
|---|---|---|---|
| 3,891,504 | 6/1975 | Schocher et al. | 435/67 |
| 3,951,742 | 4/1976 | Shepherd et al. | 435/67 |
| 3,951,743 | 4/1976 | Shepherd et al. | 435/67 |

FOREIGN PATENT DOCUMENTS

WO91/03571   3/1991   WIPO ..................... C12P 23/00

OTHER PUBLICATIONS

Iizuka, H. et al., "Microbiological Studies on Petroleum and Natural Gas: X. Carotenoid Pigment of Hydrocarbon–Utilizing Bacteria," *Journal of General and Applied Microbiology* 15(1): 127–134, 1969.

Nelis, H. L. et al. "Reinvestigation of *Brevibacterium* sp. Strain KY–4313 as a Source of Canthaxanthin," *Applied and Environmental Microbiology* 55(10): 2505–2510, 1989.

Perry et al., *J. of Bacteriology*, vol. 168, pp. 607–612, 1986.

Goodfellow et al. "Biology of the Actinomycetes".

Balows et al "The Prokaryotes", vol. II, p. 1351, Springer Verlag, 1992.

*Primary Examiner*—Irene Marx
*Attorney, Agent, or Firm*—Seed and Berry LLP

[57] ABSTRACT

Bacterium belonging to a new genus, and a process for production of carotenoid pigment selected from the group consisting of astaxanthin, adonixanthin, β-carotene, echinenone, canthaxanthin and zeaxanthin, comprising the steps of culturing a bacterium capable of producing at least one of the carotenoid pigments, and recovering an individual carotenoid pigments.

The producer bacterium belongs to new genus.

According to the present process various carotenoids can be produced in an industrial scale. By the present process (3S, 3'S)-astaxanthin can be produced in an almost 100% purity.

1 Claim, 6 Drawing Sheets

α-2, α-3, α-4, represent subclasses of Proteobacteria.
Phylogenetic Tree of E-396 and Close Species

5,607,839

BACTERIA BELONGING TO NEW GENUS PROCESS FOR PRODUCTION OF CAROTENOIDS USING SAME

BACKGROUND OF THE INVENTION

1. Field of the Invention

The present invention provides bacteria belonging to a new genus, and a process for production of carotenoids using a bacterium belonging to the new genus. The carotenoids of the present inventions are natural pigments useful for feed additives, food additives etc. Especially, astaxanthin is valuable in an industrial point of view as feed additives such as a color improver for bred fishes such as salmon, trout, red sea bream etc., and safe natural food additives. In addition, adonixanthin is, if its industrial production process is established, promising as food additives and feed additives as the astaxanthin is.

Further, β-carotene has been used as food additives, feed additives, pharmaceuticals etc., echinenone is promised as food additives, feed additives etc.; canthaxanthin has been used food additives, feed additives, cosmetics etc.; and zeaxanthin has been used as food additives, feed additives etc.

2. Related Art

It is known that astaxanthin is contained in fishes such as red sea bream, salmon, trout, etc., and Crustacea such as shrimps, crabs, crawfishes, krills (Carotenoids of Marine Organisms; edt. Nippon Suisan Gakukai, 1978). As microorganisms which produce astaxanthin, red yeast *Phaffia rhodozyma* (Phytochemistry, 15, 1009, 1976), Brevibacterium (Journal of General and Applied Microbiology, 15, 127, 1969), and green algea *Haematococcus pluvialis* (Phytochemistry, 20, 2561, 1981) are known. As chemical synthetic processes, conversion of β-carotene (Pure Appl. Chem. 57, 741, 1985) and synthesis from phosphonium salt (Helv. Chim. Acta. 64, 2436, 1981) are known.

However, the known process for production of astaxanthin are not advantageous due to high cost, because a content of astaxanthin in natural products such as krills, crawfishes, etc. is very low, and extraction thereof is difficult. In addition, stable availability of the resources is problematic. In addition, growth rate of red yeast, *Phaffia rhodozyma*, is low, productivity of astaxanthin by the red yeast is low, and extraction of astaxanthin is difficult since this yeast has hard cell wall. Therefore, industrial production of astaxanthin from the red yeast is difficult.

A growth rate of green algea, *Haematococcus pluvialis*, is also low, the culture is easily contaminated, and extraction of astaxanthin is difficult. Therefore industrial production of astaxanthin from the red algea is difficult.

It is known that adonixanthin is contained in goldfishes and carps (Carotenoids of Marine Organisms, Nippon Suisan Gakukai, 1978), but it is believed that chemical synthesis of adonixanthin is difficult. No industrial process for production of adonixanthin is known.

As production processes for β-carotene, although synthesis from β-Ionone (Pure & Appl. Chem. 63(1), 45, 1991), and extraction from green or yellow vegetables such as carrot, sweet potato, pumpkin etc. are known (Natural Coloring Agent Handbook, Korin (1979), edt. by editorial committee of Natural Coloring Agent Handbook), production cost of these processes is high. As processes for production of β-carotene by microorganisms, the production by an algea Dunaliella (J. Appl. Bacteriol., 70, 181, 1991), and the production by a fungus Blakeslea (J. Appl. Bacteriol., 70, 181, 1991) are known. However, production of β-carotene by bacteria is not known.

Echinenone is extracted from natural products, for example, starfishes such as crown-of-throns starfish, the internal organs of fishes such as red sea bream, sea urchin, the internal organs of Crustacea such as lobster, etc. (Carotenoids of Marine Organisms, edt. Nippon Suisan Gakukai, 1987). However, the production of echinenone by microorganisms is not known.

Canthaxanthin is known to be contained in a sort of mushrooms (Botanical Gazette, 112, 228–232, 1950), fishes, Crustacea etc. (Carotenoids of Marine Organisms, edt. Nippon Suisan Gakukai, 1978). The production of echinenone by microorganisms are exemplified by the production by microorganisms belonging to the genus Brevibacterium (Applied and Environmental Microbiology, 55(10), 2505, 1989), and by microorganisms belonging to the genus Rhodococcus (Japanese Unexamined Patent Publication No. 2-138996). In addition, as chemical synthetic processes, oxidation of β-carotene (J. Amer. Chem. Soc., 78, 1427, 1956) and synthesis from novel compound 3-oxo-$C_{15}$ phosphonium salt (Pure & Appl. Chem. 51, 875, 1979) are known.

As processes for production of zeaxanthin, a chemical synthesis starting from a hydroxy ketone obtained by asymmetric reduction of oxoisophorone (Pure & Appl. Chem., 63(1), 45, 1991), extraction from corn seeds (Seitai Shikiso, 1974, Asakura Shoten), and a process using Flavobacterium (Carotenoids, In Microbial Technology, 2nd edn. Vol. 1, 529–544, New York: Academic Press) are known.

SUMMARY OF INVENTION

The present invention provides bacteria belonging to a new genus.

The present inventors found that novel bacterial strains not belonging to any known genera produce various kinds of carotenoid pigments.

Accordingly, the present invention further provide a process for production of a carotenoid selected from the group consisting of astaxanthin, adonixanthin, β-carotene, echinenone, canthaxanthin and zeaxanthin comprising culturing a microorganism belonging to a new genus and capable of producing at least one of said carotenoids, and recovering a carotenoid or a combination of the carotenoids from the culture.

DETAILED DESCRIPTION OF INVENTION

Figure 1:
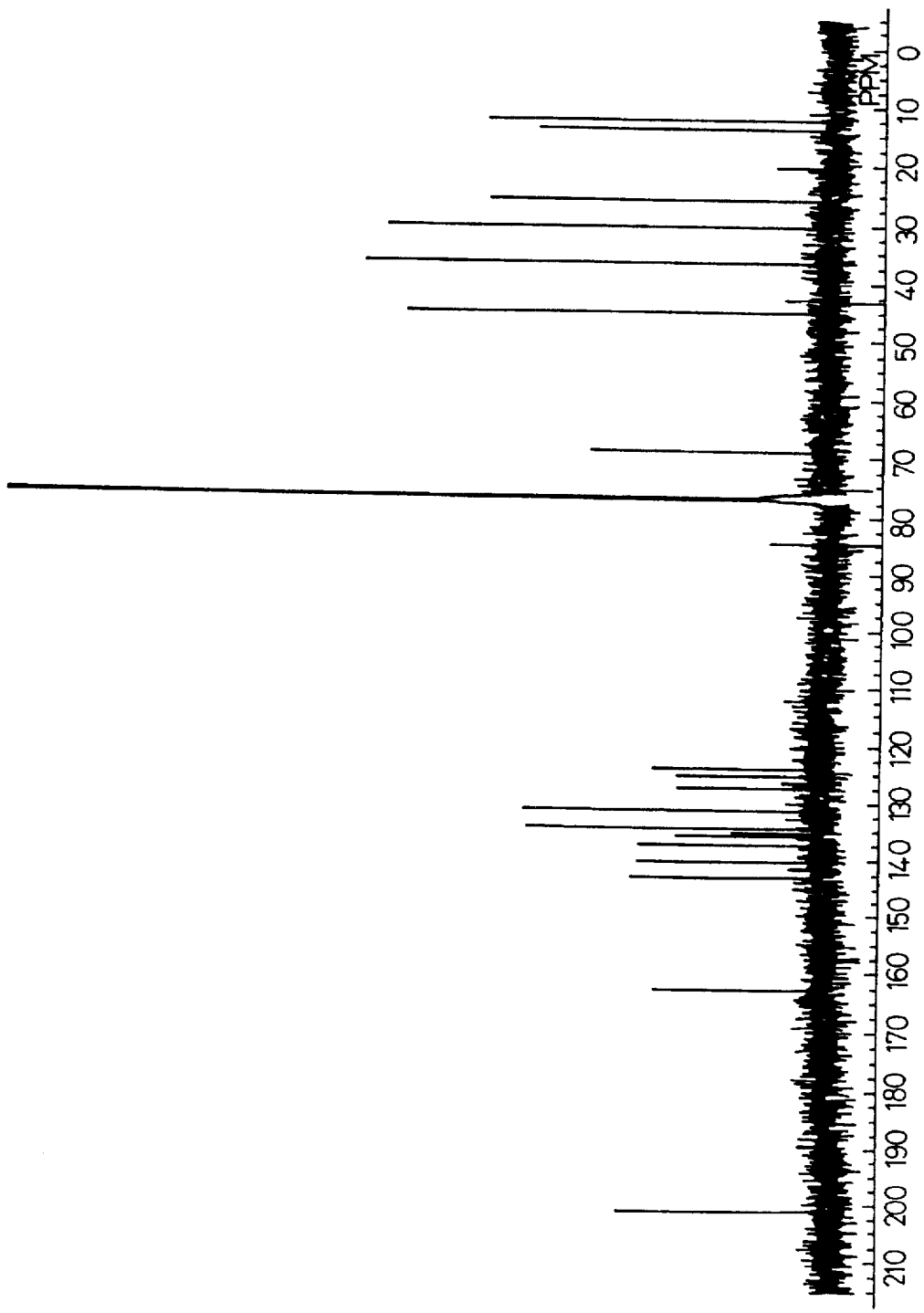
FIG. 1 shows a $^{13}$C nuclear magnetic resonance spectrum of astaxanthin produced by the present process.

The carotenoids produced according to the present invention are represented by the following formula:

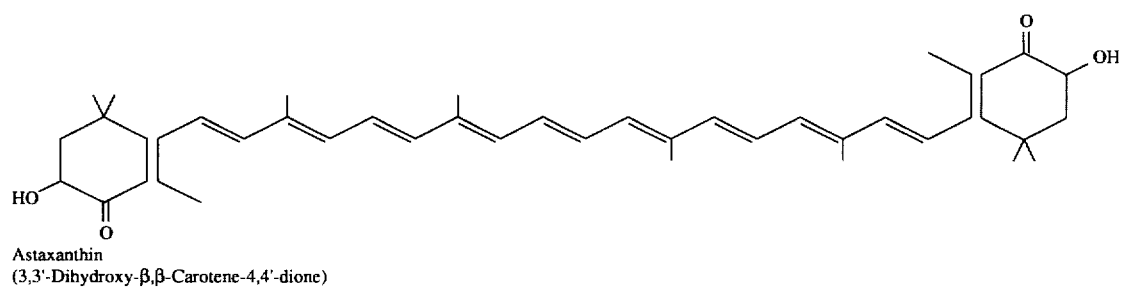

Astaxanthin
(3,3'-Dihydroxy-β,β-Carotene-4,4'-dione)

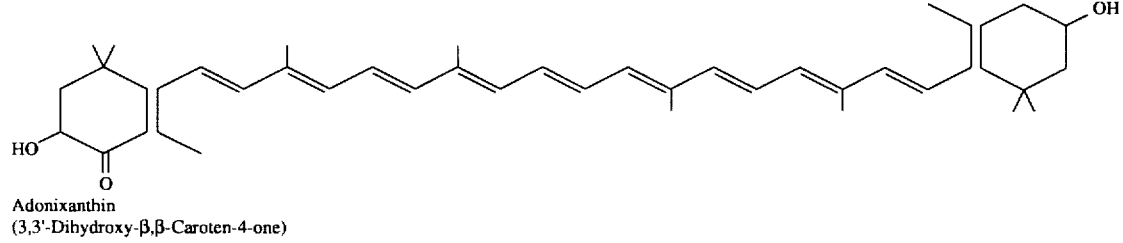

Adonixanthin
(3,3'-Dihydroxy-β,β-Caroten-4-one)

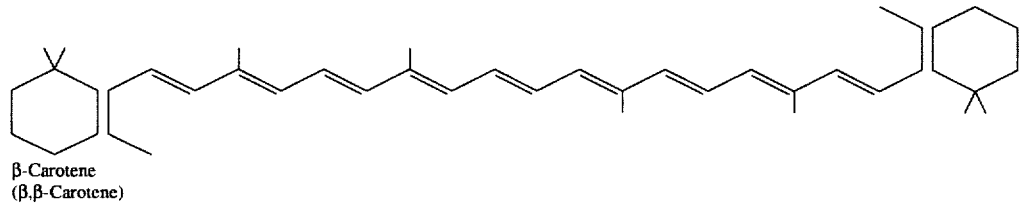

β-Carotene
(β,β-Carotene)

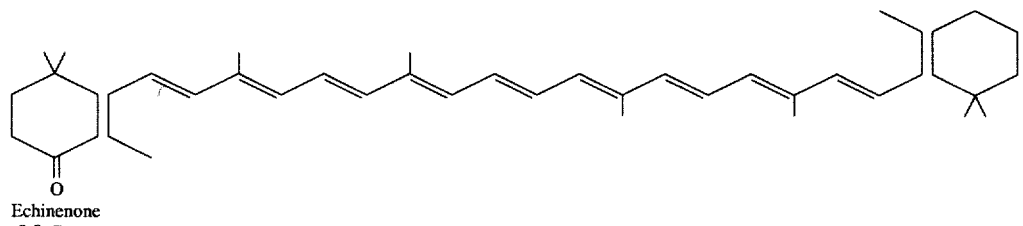

Echinenone
(β,β-Caroten-4-one)

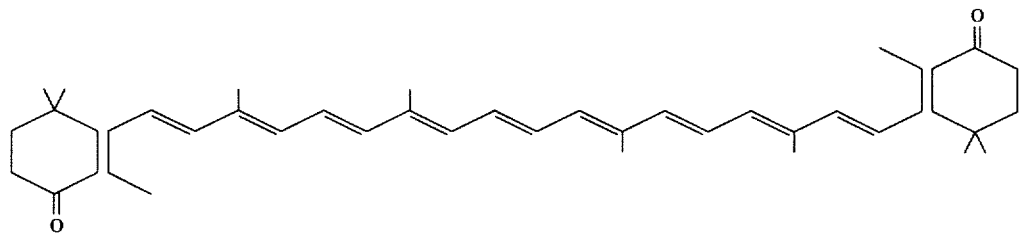

Canthaxanthin
(β,β-Carotene-4,4'-dione)

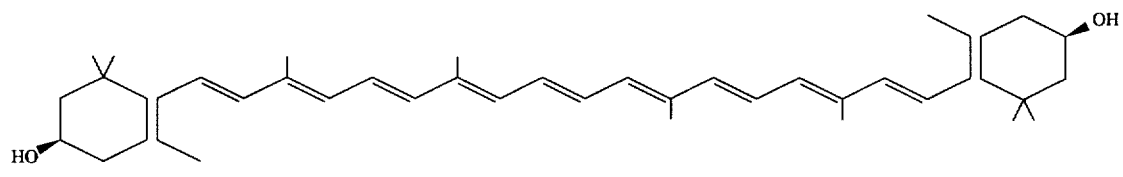

Zeaxanthin
((3R,3'R)-β,β-Carotene-3,3'-diol)

According to the present invention any bacteria capable of producing the above-mentioned carotenoids and having the following properties can be used. A group of bacteria having such properties do not belong to any of known genera described in Bergey's Manual of Systematic Bacteriology, and therefore is a group of bacteria belonging to a new genus.

| | | |
|---|---|---|
| (1) Morphology | polymorphic rod | |
| (2) Motility | motile | |
| (3) Flagella | peritricous | |
| (4) Spore formation | none | |
| (5) Gram stain | negative | |
| (6) Production of pigment | positive (water insoluble) | |
| (7) Oxidase | positive | |
| (8) Catalase | positive | |
| (9) Behavior toward oxygen | aerobic | |
| (10) Fermentation of glucose | negative | |
| (11) Production of 3-ketolactose | negative | |
| (12) Quinone type | Q-10 | |
| (13) GC content of intracellular DNA | 64–69 molar % | |
| (14) Formation of slime | | |
| Glucose | negative | |
| Sucrose | negative | |
| (15) Presence of sphingolipid | negative | |
| (16) Presence of bacteriochlorophyll | negative | |

Among those bacteria, as a particular microorganism E-396 strain can be mentioned. This strain was newly isolated by the present inventors, and has been deposited with National Institute of Bioscience and Human-Technology Agency of Industrial Science and Technology, 1-3 Higashi 1-chome, Tsukuba-shi, Ibaraki-ken Japan, on Apr. 27, 1993 as FERM BP-4283 under the Budapest Treaty.

This strain has the following properties:

(a) Morphological characters

| | | |
|---|---|---|
| (1) Shape and size of cells | | |
| rod, 0.5–0.75 × 1.0–5.0 μm | | |
| (2) Polymorphism | present | |
| (3) Motility | present, peritricious | |
| (4) Spores | none | |

(b) Cultural characters
  (1) Bouillon agar plate culture Circular orange glossy colony is formed. Diffusible pigment is not formed.
  (2) Bouillon liquid culture Growth is somewhat poor; totally cloudy; precipitated. Surface growth is not present.
  (3) Bouillon gelatin stab culture Growth is poor; gelatin is not liquefied.
  (4) Litmus milk Not changed (c) Physiological characteristics

| | | |
|---|---|---|
| (1) Gram stain | negative | |
| (2) Reduction of nitrate | negative | |
| (3) Denitrification | negative | |
| (4) MR test | negative | |
| (5) VP test | negative | |
| (6) Production of indole | negative | |
| (7) Production of hydrogen sulfide | negative | |
| (8) Hydrolysis of starch | negative | |
| (9) Utilization of citric acid | | |
| Koser medium | negative | |
| Christensen medium | negative | |
| (10) Utilization of inorganic nitrogen sources | | |
| Nitrate | negative | |
| Ammonium salt | positive | |
| (11) Production of pigment | positive (water insoluble) | |
| (12) Urease | negative | |
| (13) Oxidase | positive | |
| (14) Catalase | positive | |
| (15) Range of growth | | |
| (i) pH | growing at pH 6 to 9 (optimum pH 7) | |
| (ii) Temperature | growing at 10° C. to 33° C. (optimum 28° C.) | |
| (16) Behavior toward oxygen | aerobic | |
| (17) O-F test | oxidation (Hugh-Leifson medium supplemented with 0.1% yeast extract) | |
| (18) Formation of acid or gas from saccharides (Hugh-Leifson medium supplemented with 0.1% yeast extract) | | |

| | Acid | Gas |
|---|---|---|
| (1) L-Arabinose | + | − |
| (2) D-Xylose | + | − |
| (3) D-Glucose | + | − |
| (4) D-Mannose | + | − |
| (5) D-Fructose | − | − |
| (6) D-Galactose | + | − |
| (7) Maltose | + | − |
| (8) Sucrose | + | − |
| (9) Lactose | + | − |
| (10) Trehalose | + | − |
| (11) D-Sorbitol | + | − |
| (12) D-Mannitol | + | − |
| (13) Inositol | − | − |
| (14) Glycerin | + | − |
| (15) Starch | − | − |

(d) Other physiological characteristics

| | |
|---|---|
| (1) Decomposition of esculin | positive |
| (2) Arginine dihydrolase | negative |
| (3) Formation of 3-ketolactose | negative |
| (4) PNPG | positive |
| (5) Formation of slime | |
| Glucose | negative |
| Sucrose | negative |
| (6) Utilization (by API 20NE kit) | |
| (1) Glucose | positive |
| (2) L-Arabinose | negative |
| (3) D-Mannose | positive |
| (4) Mannitol | positive |
| (5) N-Acetyl-D-glucosamine | negative |
| (6) Maltose | positive |
| (7) Potassium gluconate | positive |
| (8) n-Capronate | negative |
| (9) Adipic acid | negative |
| (10) dl-Malic acid | positive |
| (11) Sodium citrate | negative |
| (12) Phenyl acetate | negative |

(e) Chemotaxonomic characters

| | |
|---|---|
| (1) Intracellular GC content of DNA (HPLC method) | 67 molar % |
| (2) Quinone type | Q-10 |
| (3) Bacteriochlorophyll | |
| Production in anaerobic condition | non growth |
| Production in aerobic condition | negative |
| (4) Presence of sphingolipid | negative |
| (5) Cellular fatty acid composition | |

| Fatty acid | Ratio (%) |
|---|---|
| C16:0 | 0.8 |
| C16:1 | 0.1 |
| C17:0 | 0.5 |
| C18:0 | 9.0 |
| C18:1 | 81.4 |

| | |
|---|---|
| C19:0 | 0.4 |
| 2-OH C14:0 | 0.2 |
| 3-OH C14:0 | 0.6 |

(6) DNA-DNA homology with analogous species (HPLC method)

| Strains tested | Homology (%) |
|---|---|
| *Flavobacterium okeanokoites* IFO 12536 | 2 |
| *Flavobacterium resinovorum* ATCC 33545 | 23 |
| *Flavobacterium aquatile* IFO 15052 | 0 |
| *Agrobacterium tumefaciens* IFO 15193 | 0 |
| *Agrobacterium radiobacter* IFO 12532 | 7 |
| *Mycoplana bullata* IFO 13290 | 32 |
| *Mycoplana segnis* IFO 15250 | 26 |
| *Mycoplana ramosa* IFO 15249 | 9 |
| *Mycoplana dimorpha* IFO 13291 | 11 |
| *Xanthobacter flavus* IFO 14759 | 24 |
| *Sphingomonas paucimobilis* IFO 13935 | 6 |

(7) Nucleotide sequence of DNA coding for 16S ribosome RNA Shown in SEQ ID:1

From the above result, the strain E-396 was considered to be a bacterium belonging to the genus Aqrobacterium since it is aerobic, gram negative and peritricous rod, but this was negated due to the results of pigment productivity, slime-forming ability and DNA-DNA homology. In addition, the strain was considered to be a bacterium belonging to the genus Sphinqomonas or a photosynthesis bacterium from the color of colony, but they were also negated because sphingolipid and bacteriochlorophyll were not detected.

Some stored strains assumed to be close to the strain E-396 in the similarity of colony color, peritricous flagella, GC content and quinone type were selected, and DNA-DNA homology between the strain E-396 and the selected strains was tested. As a result, there is no genus which shows the similarity to the strain E-396 in the DNA-DNA homogoly. In addition, a phylogenetic tree was prepared on the basis of the nucleotide sequence of 16S ribosome RNA of the strain E-396 according to the neighbor-joing method. As a result, it was found that the strain E-396 is independent from any close genus. Therefore it was confirmed that the strain E-396 is a bacterium belonging to a new genus but not belonging to any known genus.

As further particular microorganism, the strain A-581-1 is mentioned. This strain was newly isolated by the present inventors, and has been deposited with National Institute of Bioscience and Human Technology Agency of Industrial Science and Technology, 1-3 Higashi 1-chome, Tsukuba-shi, Ibaraki-ken Japan, on May 20, 1994 as FERM BP-4671 under the Budapest Treaty.

This strain has the following properties:

(a) Morphological characters

| | | |
|---|---|---|
| (1) | Shape and size of cell rod, 0.5–1.0 × 3.5 μm | |
| (2) | Polymorphism | present |
| (3) | Motility | present, peritricous |
| (4) | Spores | none |

(b) Cultural characters
  (1) Bouillon agar plate culture Circular orange glossy colony is formed. Diffusible pigment is not formed.
  (2) Bouillon liquid culture Totally cloudy; precipitated. Surface growth is not present.
  (3) Bouillon gelatin stab culture Growth is poor; gelatin is not liquefied.
  (4) Litmus milk Not changed (c) Physiological characteristics

| | | |
|---|---|---|
| (1) | Gram stain | negative |
| (2) | Reduction of nitrate | negative |
| (3) | Denitrification | negative |
| (4) | MR test | negative |
| (5) | VP test | negative |
| (6) | Production of indole | negative |
| (7) | Production of hydrogen sulfide | negative |
| (8) | Hydrolysis of starch | negative |
| (9) | Utilization of citric acid | |
| | Koser medium | negative |
| | Christensen medium | negative |
| (10) | Utilization of inorganic nitrogen sources | |
| | Nitrate | negative |
| | Ammonium salt | positive |
| (11) | Production of pigment | positive (water insoluble) |
| (12) | Urease | negative |
| (13) | Oxidase | positive |
| (14) | Catalase | positive |
| (15) | Range of growth | |
| | (i) pH | growing at pH 6 to 10 (optimum pH 8) |
| | (ii) Temperature | growing at 10° C. to 33° C. (optimum 28° C.) |
| (16) | Behavior toward oxygen | aerobic |
| (17) | O–F test | oxidation (Hugh-Leifson medium supplemented with 0.1% yeast extract) |
| (18) | Formation of acid or gas from saccharides (Hugh-Leifson medium supplemented with 0.1% yeast extract) | |

| | | Acid | Gas |
|---|---|---|---|
| (1) | L-Arabinose | + | − |
| (2) | D-Xylose | + | − |
| (3) | D-Glucose | + | − |
| (4) | D-Mannose | + | − |
| (5) | D-Fructose | + | − |
| (6) | D-Galactose | + | − |
| (7) | Maltose | + | − |
| (8) | Sucrose | + | − |
| (9) | Lactose | + | − |
| (10) | Trehalose | + | − |
| (11) | D-Sorbitol | − | − |
| (12) | D-Mannitol | + | − |
| (13) | Inositol | − | − |
| (14) | Glycerin | + | − |
| (15) | Starch | − | − |

(d) Other physiological characteristics

| | | |
|---|---|---|
| (1) | Decomposition of esculin | positive |
| (2) | Arginine dihydrolase | negative |
| (3) | Formation of 3-ketolactose | negative |
| (4) | PNPG | positive |
| (5) | Formation of slime | |
| | Glucose | negative |
| | Sucrose | negative |
| (6) | Utilization (by API 20NE kit) | |
| | (1) Glucose | positive |
| | (2) L-Arabinose | positive |
| | (3) D-Mannose | negative |
| | (4) Mannitol | positive |
| | (5) N-Acetyl-D-glucosamine | negative |
| | (6) Maltose | negative |
| | (7) Potassium gluconate | negative |
| | (8) n-Capronate | negative |
| | (9) Adipic acid | negative |
| | (10) dl-Malic acid | positive |
| | (11) Sodium citrate | negative |

|   |   |   |
|---|---|---|
| | (12) Phenyl acetate | negative |
| (e) | Chemotaxonomic characters | |
| | (1) Intracellular GC content of DNA (HPLC method) | 66 molar % |
| | (2) Quinone type | Q-10 |
| | (3) Bacteriochlorophyll | |
| | Production in anaerobic condition | non growth |
| | Production in aerobic condition | negative |
| | (4) Presence of sphingolipid | negative |
| | (5) DNA—DNA homology with the strain E-396 (HPLC method) | homology 56% |

From the above results as well as the facts that the strains A-581-1 has the following characteristics as the strain E-396 has, and that the strain A-581-1 has high DNA-DNA homology with the strain E-396, it is determined that the strain A-581-1 belongs to the new genus to which the strain E-396 also belongs.

|   |   |
|---|---|
| (1) Morphology | polymorphic rod |
| (2) Motility | motile |
| (3) Flagella | peritricous |
| (4) Spore formation | none |
| (5) Gram stain | negative |
| (6) Production of pigment | positive (water insoluble) |
| (7) Oxidase | positive |
| (8) Catalase | positive |
| (9) Behavior toward oxygen | aerobic |
| (10) Fermentation of glucose | negative |
| (11) Production of 3-ketolactose | negative |
| (12) Quinone type | Q-10 |
| (13) GC content of intracellular DNA | 64–69 molar % |
| (14) Formation of slime | |
| Glucose | negative |
| Sucrose | negative |
| (15) Presence of sphingolipid | negative |
| (16) Presence of bacteriochlorophyll | negative |

Medium for production of carotenoids using the present microorganisms is, for example, as follow. Namely, it contains a carbon source, a nitrogen source and inorganic salts necessary for the growth of producer microorganisms, as well as if necessary special required substances (for example, vitamines, amino acids, nucleic acids etc.). As the carbon sources, sugars such as glucose, sucrose, lactose, fructose, trehalose, mannose, mannitol, maltose, etc., organic acids such as acetic acid, fumaric acid, citric acid, propionic acid, malic acid, pyruvic acid, malonic acid; alcohols such as ethanol, propanol, butanol, pentanol, hexanol, isobutanol, glycerol; oil or fat such as soybean oil, rice bran oil, olive oil, corn oil, sesame oil, linseed oil, and the like are mentioned. Amount of the carbon source added varies according to the kind of the carbon source, and usually 1 to 100 g, preferably 2 to 50 g per 1l medium.

As the nitrogen sources, for example, potassium nitrate, ammonium nitrate, ammonium chloride, ammonium sulfate, ammonium phosphate, ammonia, urea etc. are used alone or in combination. Amount of the nitrogen source added varies according to the kind of the nitrogen source, and usually 0.1 to 30 g, and preferably 1 to 10 g per 1l medium.

As the inorganic salts, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc chloride, cupric sulfate, calcium chloride, calcium carbonate, sodium carbonate etc. may be used alone or in combination. Amount of inorganic acid varies according to the kind of the inorganic salt, and usually 0.001 to 10 g per 1l medium.

As special required substances, vitamines, nucleic acids, yeast extract, peptone, meat extract, malt extract, corn steep liquor, soybean meal, dried yeast etc. may be used alone or in combination.

Amount of the special required substance used varies according to the kind of the substance, and usually 0.2 g to 200 g, and preferably 3 to 100 g per 1l medium. A pH value of a medium is adjusted to pH 2 to 12, preferably 6 to 9. Culturing is carried out at temperature of 15 to 80° C., and preferably 20° to 35° C., usually for 1 to 20 days, and preferably 2 to 8 days, under an aerobic condition provided by shaking or aeration/agitation.

Finally the present compound may be isolated and purified from the culture. Namely, microbial cells are separated from the culture by a conventional means such as centrification or filtration, and the cells are subjected to an extraction with a solvent. Since a small amount of carotenoids is dissolved in a supernatant or filtrate, the carotenoids also may be recovered from them. As a solvent for the extraction, any substance in which the present compound is soluble can be used. For example, organic solvents such as a acetone, chloroform, dichloromethane, hexane, cyclohexane, methanol, ethanol, isopropanol, benzene, carbon disulfide, diethyl ether etc. are used, and preferably chloroform, dichloromethane, acetone, methanol, ethanol or isopropanol is used. The purification can be carried out by conventional procedures such as absorption, elution, dissolving and the like, alone or preferably in combination.

According to the present invention, in many cases, astaxanthin, adonixanthin, β-carotene, echinenone, canthaxanthin and zeaxanthin are simultaneously produced and present in a culture product. Accordingly, in an embodiment of the present invention, any one of the above-mentioned carotenoids can be singly obtained by the above-mentioned procedure. Alternatively, a mixture of the carotenoids also can be obtained. In this way, the process for carotenoid production of the present invention includes a process for production of an individual carotenoid and a process for production of a mixture of the carotenoids.

Astaxanthin and adonixanthin can be separated from each other according to a conventional procedure for mutual separation of carotenoids, such as adsorption/elusion column chromatography, differential extraction, counter current extraction, differential crystallization.

In addition, for production of an individual carotenoid, the desired carotenoid may be preferentially produced by controlling medium composition, culture conditions and the like.

For example, a ratio of carotenoids produced can be changed by changing an aerobic condition. For example, a ratio of carotenoids produced may be changed by an amount of a medium or a rate of shaking in flask-shaking culture, or by changing a rate of air supply or a rate of agitation in aeration/agitation culture. As a particular example, there is a tendency in flask culture that an amount of astaxanthin produced increases, while an amount of adonixanthin decreases, as a volume of a culture medium in a flask increases.

Alternatively, for preferential production of a particular carotenoid, a producer microorganism can be improved by a mutation such as artificial mutation of the producer microorganism so that a mutant microorganism preferentially produces the desired carotenoid among others. Such mutation treatments include, for example, physical methods such as X-ray radiation, UV radiation and the like; chemical methods such as the use of N-methyl-N'-nitro-N-nitrosoguanidine (NTG), ethylmethane sulfonate (EMS); and a biological methods such as gene recombination technique. Processes for production of the carotenoids using such an improved mutant is included in the present process for production of carotenoids.

In astaxanthin produced by the present process as described above, purity of (3S, 3'S)-astaxanthin is almost 100%. It is known that a ratio of (3S, 3'S)-astaxanthin in astaxanthin contained in natural products such as crawfish, Haematococcus, salmon, trout, red sea bream is high. On the other hand, it is known that *Phaffia rhodozyma* contains (3R, 3'R)-astaxanthin in a high ratio, which absolute configuration is the opposite of that of astaxanthin contained in most of natural products.

Almost 100% of astaxanthin produced by the present process is (3S, 3'S)-astaxanthin whose absolute configuration is same as that of a majority of naturally occurring astaxanthin, and therefore astaxanthin produced by the present process is industrially valuable. In addition, although chemical synthesis of (3S, 3'S)-astaxanthin is known (Helv. Chim. Acta, 61, 2609, 1978), since optically pure (4R, 6R)-4-hydroxy-2,2,6-trimethylcyclohexanone is used as a starting material, the process is of high cost, and industrially not advantageous.

In addition, astaxanthin produced by the present process contains all-trans astaxanthin in a high ratio, with a ratio of all-trans form:cis form being 92:8 to 96:4. The all-trans astaxanthin is of natural form, and the present producer microorganisms are advantageous in that they produce natural type astaxanthin. Where cis-astaxanthin is necessary, this can be obtained from all-trans astaxanthin according to a known process, while it is difficult to prepare all-trans astaxanthin from cis-astaxanthin.

Figure 2:
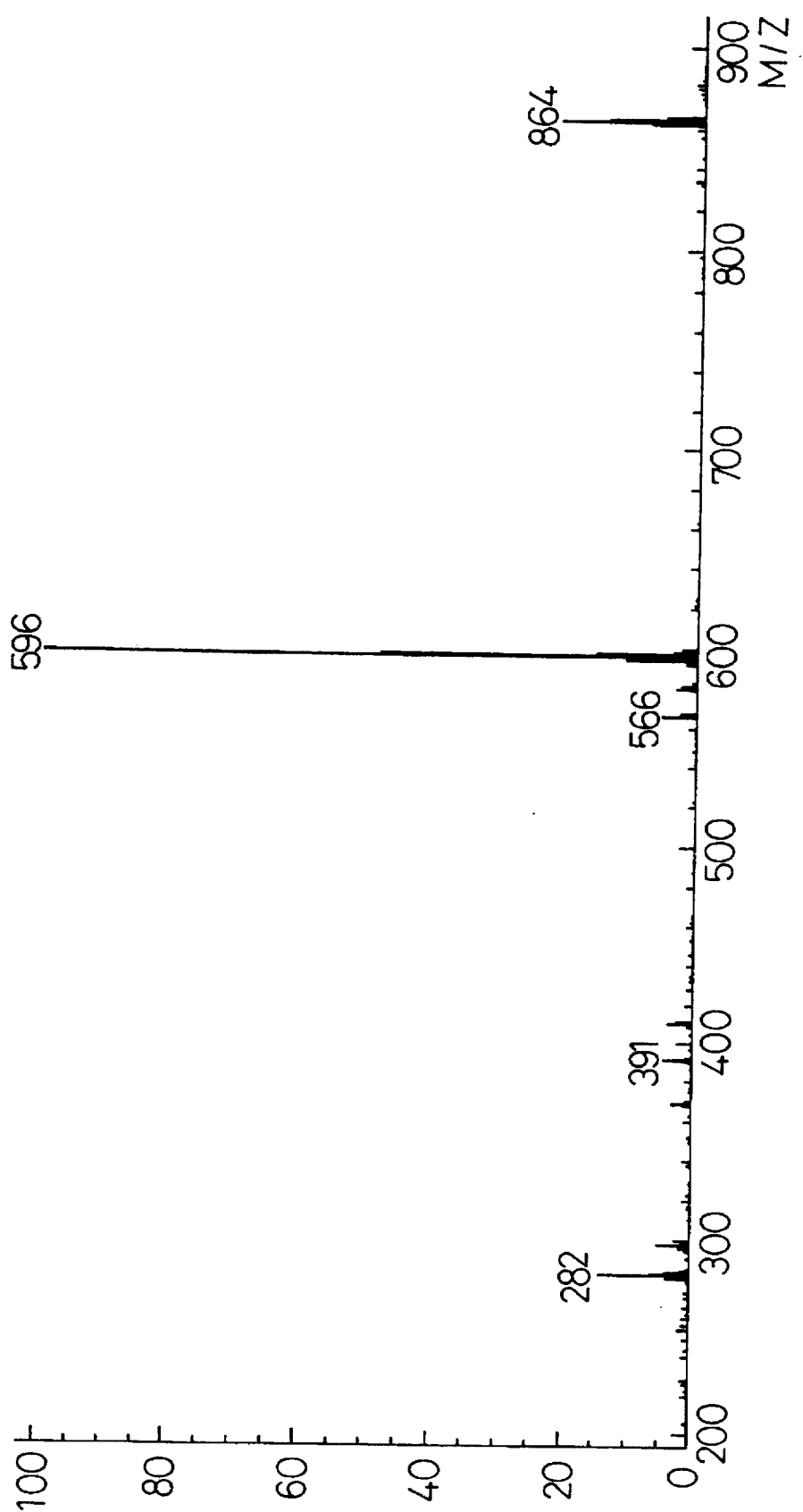
FIG. 2 shows a mass spectrum of astaxanthin produced by the present process.
Figure 3:
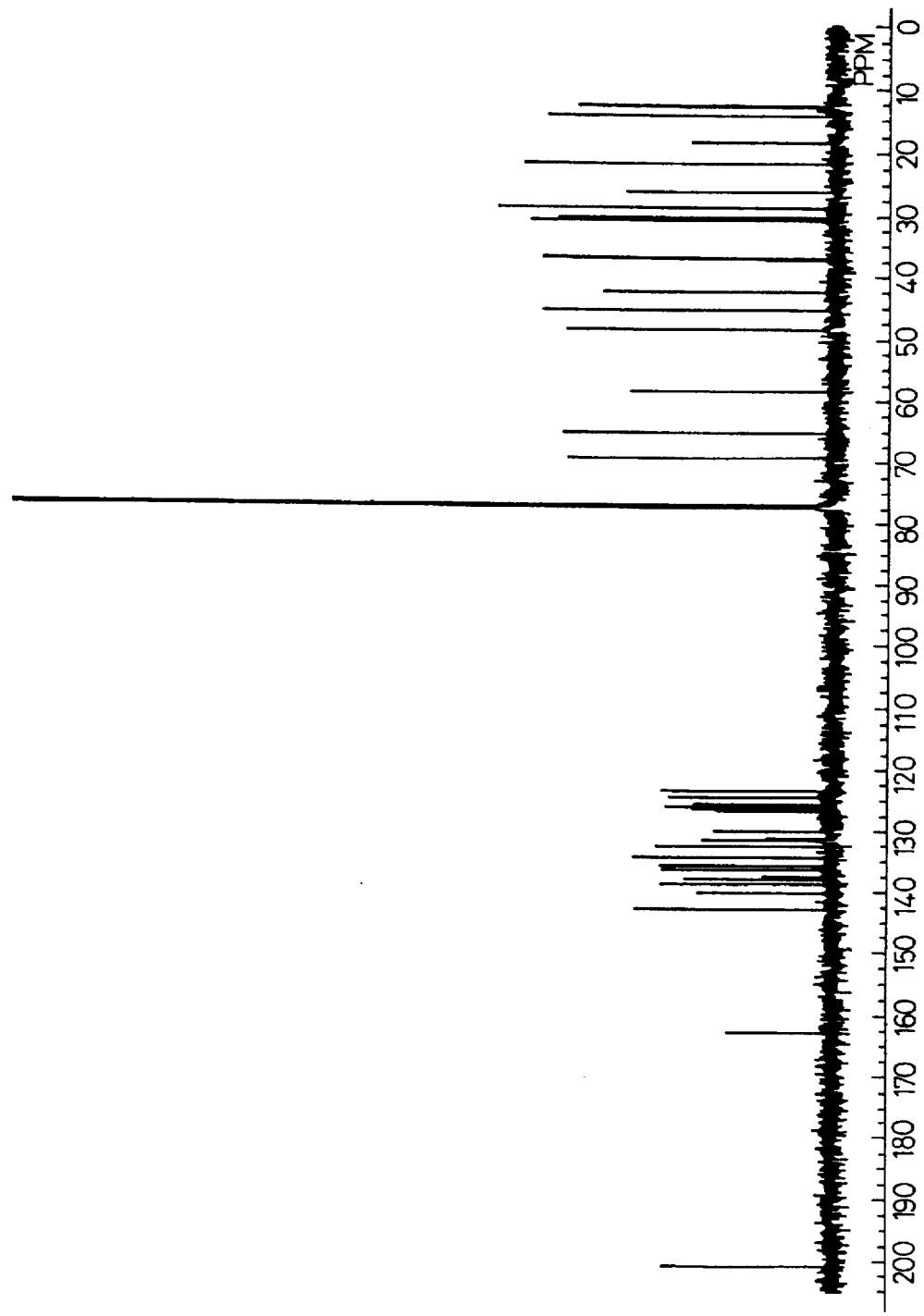
FIG. 3 shows a $^{13}$C nuclear magnetic resonance of adonixanthin produced by the present process.
Figure 4:
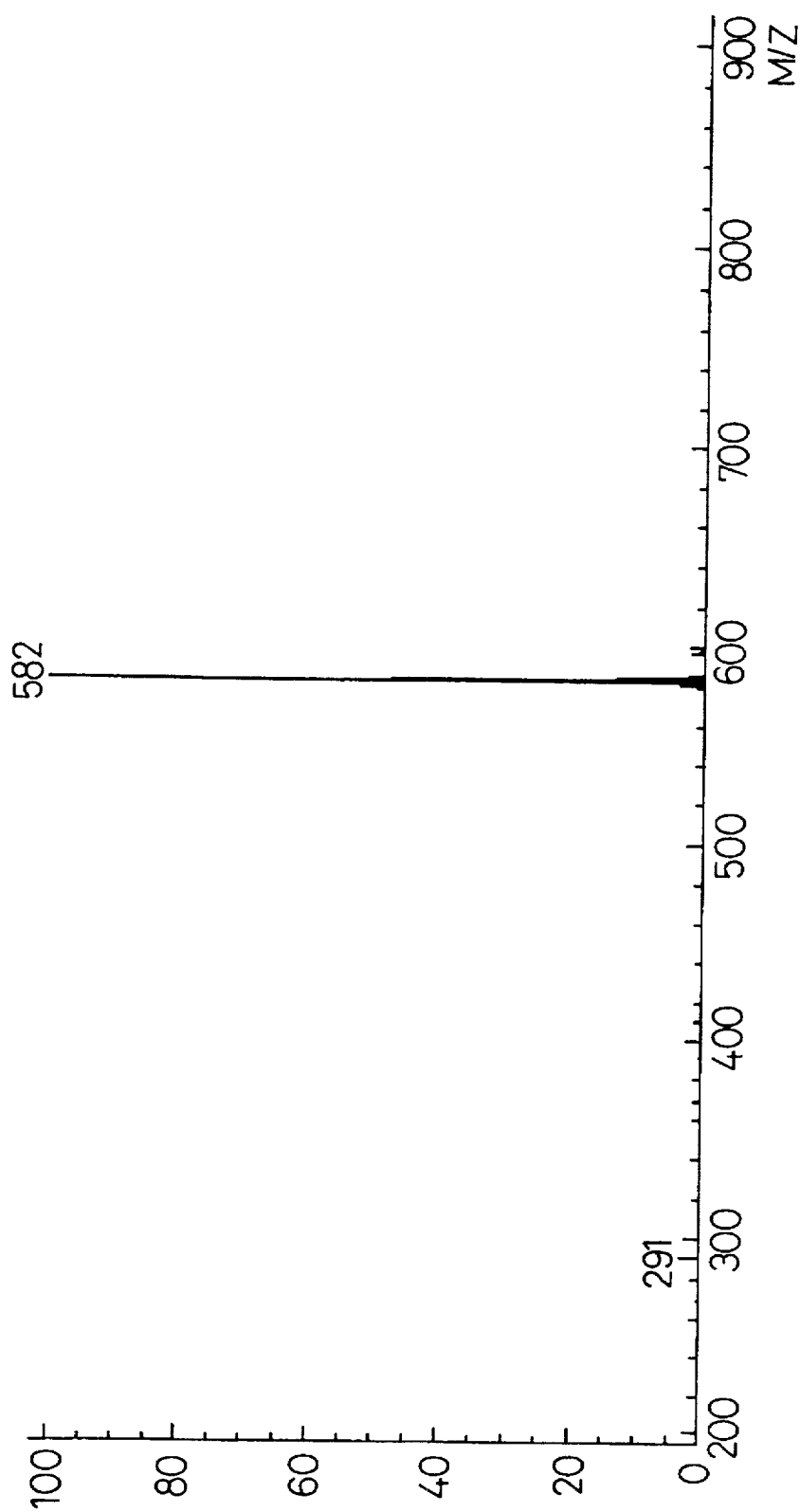
FIG. 4 shows a mass spectrum of adonixanthin produced by the present process.
Figure 5:
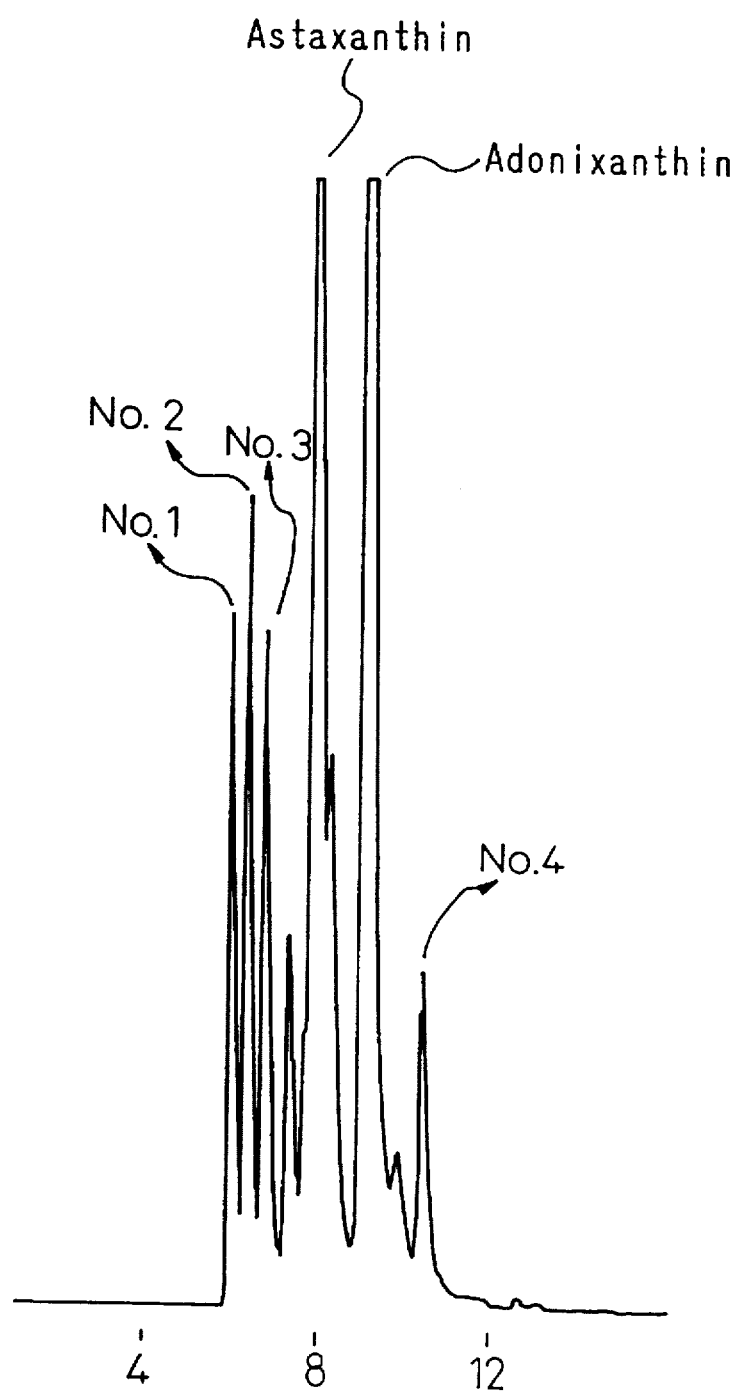
FIG. 5 shows a profile of elution of carotenoid pigments of the present invention in a high performance liquid chromatography.
Figure 6:
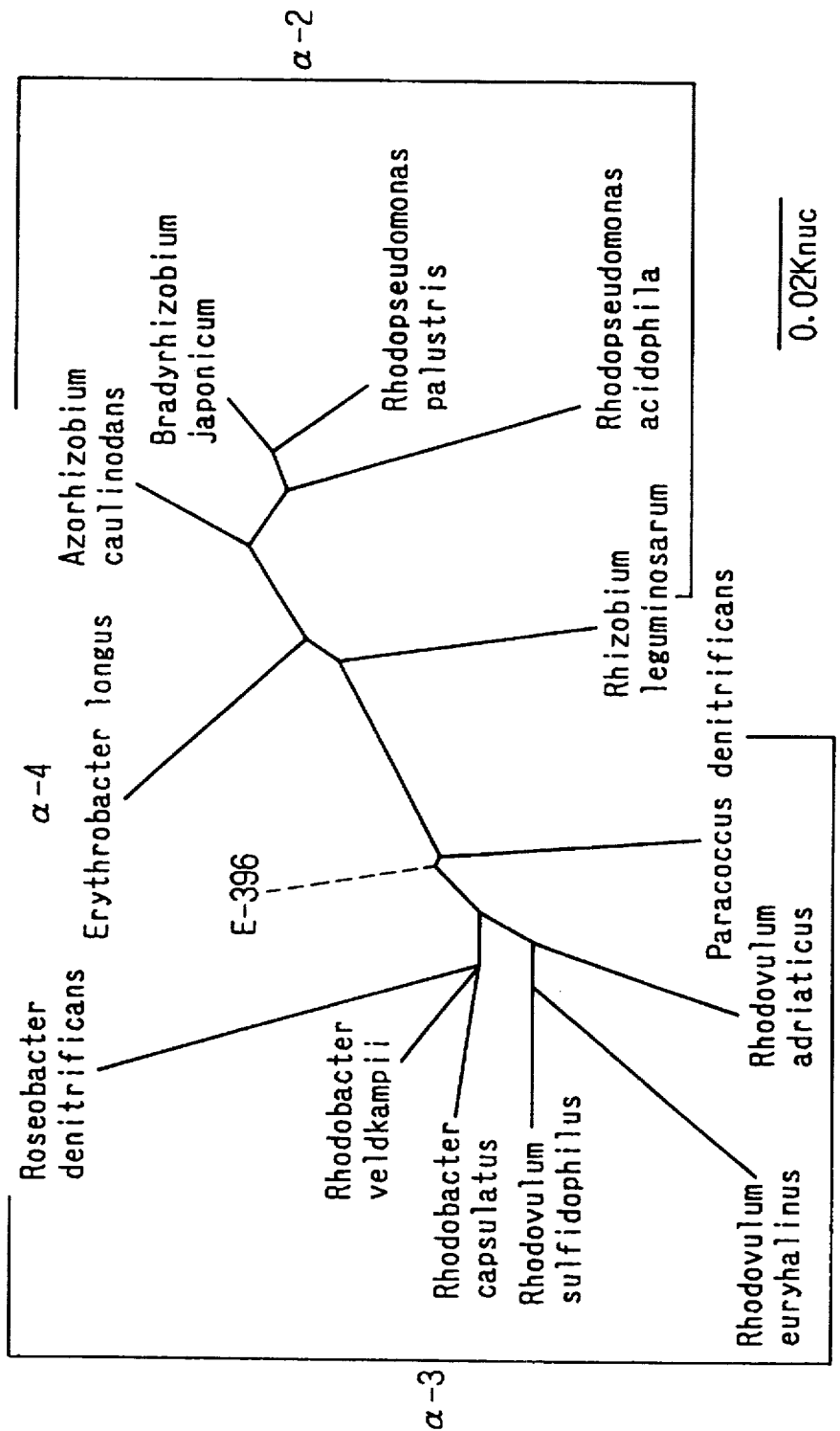
FIG. 6 shows a phylogenetic tree of E-396 strain and close species.

$^{13}$C nuclear magnetic resonance spectrum and mass spectrum of the astaxanthin produced by the present process are shown in FIGS. 1 and 2 respectively. $^{13}$C nuclear magnetic resonance spectrum and mass spectrum of adonixanthin produced by the present process are shown in FIGS. 3 and 4 respectively.

EXAMPLES

Next, the present invention is explained by Examples. However the scope of the present invention should not be limited to the Examples.

Example 1

One gram of soil obtained in Midori-ku, Kanagawa-prefecture, Japan was suspended in 5 mL of sterilized physiological saline, the supernatant was diluted 100 fold and plated on a buillon agar plate medium, followed by culturing at 30° C. for 3 days. Colonies with orange color were selected so as to obtain a strain E-396 (FERM BP-4283).

From the above-described taxonomical properties, it is confirmed that the strain E-396 (FERM BP-4283) is a bacterium belonging to a new genus.

Example 2

One gram of soil obtained in Midori-ku, Kanagawa-prefecture, Japan was suspended in 5 mL of sterilized physiological saline, the supernatant was diluted 100 fold and plated on a buillon agar plate medium, followed by culturing at 30° C. for 5 days. Colonies with orange color were selected so as to obtain a strain A-581-1 (FERM BP-4671).

From the above-described taxonomical properties, it is determined that the strain A-581-1 (FERM BP-4671) has the similar properties as the E-396 and belongs to the new genus to which the strain E-396 belongs, because the A-581-1 has high DNA-DNA homology with the E-396.

Example 3

Ten ml of a medium containing 2 g/L glucose, 3 g/L meat extract, 10 g/L pepton and 5 g/L sodium chloride was put into a test tube having a diameter of 18 mm, which was then autoclaved at 121° C. for 15 minutes. A piece of cells of E-396 strain (FERM BP-4283) was inoculated into the medium, and cultured at 30° C. for 6 days at 300 rpm with shaking. 100 tubes of the cultured broth (1L) was centrifuged to obtain cells which were then extracted with 500 ml of acetone, and to the separated acetone layer were added 500 mL of hexane and 500 mL of 0.85% saline, and the whole was mixed. The upper layer is recovered, and the solvent was evaporated off at 35° C. under a reduced pressure.

The extract thus obtained was adsorbed on a silica gel column, and eluted with a mixture of benzene/ethyl acetate/methanol (15:4:1) to obtain an astaxanthin fraction, from which then the solvent was evaporated off under a reduced pressure. The extract was dissolved in a small amount of pyridin, and water was dropwise added to the pyridin solution to crystallize astaxanthin, and 1.2 mg of crystallin astaxanthin was obtained. Astaxanthin thus obtained was identical with authentic astaxanthin in its IR spectrum, mass spectrum, $^{13}$C nuclear magnetic resonance spectrum and absorption spectrum.

Example 4

Ten ml of a medium having the composition as shown in Table 1 was put into each of test tubes having a diameter of 18 mm, and autoclaved at 121° C. for 15 minutes.

TABLE 1

| Composition | Amount added |
| --- | --- |
| Yeast extract | 20 g/L |
| Sucrose | 10 g/L |
| KH$_2$PO$_4$ | 1.5 g/L |
| Na$_2$HPO$_4$ | 1.5 g/L |
| MgSO$_4$.7H$_2$O | 0.5 g/L |
| FeSO$_4$.7H$_2$O | 0.01 g/L |
| CaCl$_2$.2H$_2$O | 0.01 g/L |
| pH 7.0 (adjusted with Na$_2$CO$_3$) | |

A piece of cells of E-396 (FERM BP-4283) was inoculated into the tubes and cultured at 30° C. for 2 days with reciprocating shaker at 300 rpm. 10 ml of the culture was inoculated into 100 ml of a medium having the same composition as described above, in a 500 mL Sakaguchi flask, and reciprocating culturing at 100 rpm was carried out at 30° C. for 2 days. Next, 100 ml of the culture thus prepared was inoculated into 3.0 L of a medium having the same composition as described above in a 5.0 L fermentor, and culturing was aerobically carried out at 30° C. and 1.0 vvm for 52 hours.

Next, 3 L of the culture was inoculated into 35 L of a medium having the same composition as described above (except that 10 g/L yeast extract, 20 g/L sucrose and 2.5 g/L $NH_4NO_3$ were used) in a 50 L fermentor, and culturing was aerobically carried out at 30° C., 250 rpm and 1.0 vvm for 18 hours. 33 L of the cultured broth thus obtained was centrifuged to obtain 790 g of wet cells, which were then washed with 1.3 L of methanol and extracted three times with 0.8 L of chloroform. Astaxanthin was purified from the pigment extract according to the same procedure as described in Example 3 to obtain 10 mg of crystalline astaxanthin.

The astaxanthin thus obtained conformed to an authentic astaxanthin in its IR spectrum, mass spectrum $^{13}C$ nuclear magnetic resonance spectrum, and absorption spectrum. In addition, the absolute configuration of astaxanthin thus obtained was determined by known method (J. High Resolut. Chromatogr. Chromatogr Commun., 2, 195, 1979). As a result, 100% of astaxanthin was (3S, 3'S)-astaxanthin, and a ratio of all-trans-astaxanthin and cis-astaxanthin was 95:5. For the purpose of comparison, a result of analysis for astaxanthin produced by other processes was shown in Table 2.

TABLE 2

|  | 3R, 3'R form | meso form | 3S, 3'S form |
|---|---|---|---|
| Product by E-396 | 0.0% | 0.0% | 100.0% |
| Carophyll pink, Roche | 24.8% | 50.2% | 25.0% |
| Extract from crawfish | 17.6% | 28.4% | 53.9% |

Example 5

Ten mL of a medium having the same composition as shown in Table 1 (except that 30 g/L sucrose was used) was put into each of test tubes having a diameter of 18 mm, and autoclaved at 121° C. for 15 minutes. A piece of cells of E-396 (FERM BP-4283) was inoculated into the medium and cultured at 25° C. for 5 days with reciprocating at 300 rpm. 10 mL of the culture was centrifuged to obtain cells, which were then extracted with 10 mL of acetone. To the separated acetone layer, were added 10 ml of hexane and 10 ml of 0.85% saline, and the upper layer was recovered and the solvent was evaporated off at 35° C. under a reduced pressure.

The pigment extract thus obtained was analysed for its carotenoid content by a high performance liquid chromatography, and a result shown in Table 3 was obtained. The analytical condition was as follows: A column was prepared by linking two Wakosil 5SIL-120 columns (Wako Pure Chemical) of 4.6 mm I.D×250 mm, and the mobile phase was a mixture of hexane/dichloromethane/methanol (10:8:1). Detection of carotenoids was carried out by absorption at 470 nm, and quantitative analysis was carried out by comparing an area of the peak of astaxanthin in a test sample and that of an authentic preparation. In addition, the absolute configuration of astaxanthin was determined in accordance with the same procedure as described above. As a result, 100% of astaxanthin produced was (3S, 3'S)-astaxanthin, and a ratio of all-trans form and cis form was 95:5.

TABLE 3

| Astaxanthin mg/L | Adonixanthin mg/L | Total carotenoids mg/L |
|---|---|---|
| 19.4 | 13.5 | 61.9 |

Example 6

Ten mL of a medium having the same composition as shown in Table 1 (except that 30 g/L sucrose was used) was put into each of test tubes having a diameter of 18 mm, and autoclaved at 121° C. for 15 minutes. A piece of cells of E-396 (FERM BP-4283) was inoculated into the medium, and cultured at 25° C. for 2 days with reciprocating at 300 rpm. The culture was inoculated at an amount of 1% by volume into different volumes between 25 ml and 200 ml of media having the same composition as described above in 500 ml conical flasks, and rotary shaking culture was carried out at 25° C., for 5 days at 120 rpm. Extraction and analysis of carotenoids from the culture broths were carried out according to the same procedure as described in Example 5. Amounts of astaxanthin, adonixanthin and total carotenoids are shown in Table 4.

TABLE 4

| Volume of Medium in conical flask mL | Astaxanthin mg/l | Adonixanthin mg/L | Total carotenoids mg/L |
|---|---|---|---|
| 25 | 5.6 | 56.2 | 63.3 |
| 50 | 16.4 | 31.5 | 76.2 |
| 100 | 6.8 | 20.9 | 53.4 |
| 200 | 11.6 | 5.8 | 34.7 |

Example 7

The pigment extract obtained in Example 4 was adsorbed on a silica gel column, and an adonixanthin fraction was eluted with a mixed solvent of benzene, ethyl acetate and methanol (15:4:1), and the solvent was evaporated off under a reduced pressure. The extract was dissolved in ethanol at 50° C., and the solution was allowed to stand at 4° C. for one day to crystallize adonixanthin. 190 mg of crystalline adonixanthin was obtained. The adonixanthin thus obtained conformed to authentic adonixanthin in its IR spectrum, mass spectrum, $^{13}C$ NMR spectrum and absorption spectrum.

Example 8

Ten mL of a medium having the same composition as shown in Table 1 (except that 30 g/L sucrose was used) was put into each of test tubes having a diameter of 18 mm, and autoclaved at 121° C. for 15 minutes. A piece of cells of E-396 (FERM BP-4283) was inoculated into the medium and cultured at 28° C. for 5 days with shaking. Carotenoids were extracted from the culture according to the same procedure as described in Example 5, and the carotenoids were analyzed by a high performance liquid chromatography. Elution time of each peak and the wave length at the maximum absorption of each peak in the same solvent as elute are shown in Table 5.

TABLE 5

Elution time and wave length of maximum absorption for each peak

| Peak No. | Elution time (min) | λmax nm |
|---|---|---|
| No. 1 | 6.0 | (428) 456 481 |
| No. 2 | 6.3 | 464 |
| No. 3 | 6.8 | 474 |
| No. 4 | 10.4 | (426) 455 482 |

Elution time and wave length of maximum absorption were measured for authentic β-carotene and canthaxanthin according to the same procedure as described above. As a result, the measurements of the peak No. 1 and peak No. 3 well conformed to those of β-carotene and canthaxanthin respectively. Therefore, the peak No. 1 and peak No. 3 were identified as those representing β-carotene and canthaxanthin respectively. In addition, other peaks were compared with the maximum absorption peaks described in Davies B. H. 1976, Carotenoids, 38–165, In T. W. Goodwin (ed.), Chemistry and Biochemistry of Plant Pigments, Vol. 2, Academic Press, Inc. (London), Ltd., London. As a result, the peak No. 2 and the peak No. 4 were identified as those representing echinenone and zeaxanthin respectively.

Example 9

Ten mL of brain heart infusion bouillon medium (Eiken Chemical Co., Ltd., pH value was adjusted to 10 with $Na_2CO_3$) was put into each of test tubes having a diameter of 18 mm, and autoclaved at 121° C. for 15 minutes. A piece of cells of A-581-1 strain (FERM BP-4671) was inoculated into the medium and cultured at 33° C. for 4 days with shaking. Carotenoids were extracted from the culture, and quantitatively analyzed by high performance liquid chromatography, according to the same procedure as described in Example 5. A result is shown in Table 6.

TABLE 6

| Astaxanthin mg/L | Adonixanthin mg/L | Total carotenoids mg/L |
|---|---|---|
| 0.30 | 0.45 | 0.72 |

In addition, the absolute configuration of astaxanthin thus obtained was determined according to the same procedure as described in Example 4, and it was confirmed that 100% of astaxanthin produced was (3S, 3'S)-astaxanthin, and that a ratio of all-trans astaxanthin and cis-astaxanthin was 95:5. A result is shown in Table 7.

TABLE 7

| 3R, 3'R form | meso form | 3S, 3'S form |
|---|---|---|
| 0.0% | 0.0% | 100.0% |

Example 10

Ten mL of a medium having the composition shown in Table 8 was put into each of test tubes having a diameter of 18 mm, and autoclaved at 121° C. for 15 minutes.

TABLE 8

| Composition | Amount added |
|---|---|
| Glucose | 10 g/L |
| Polypepton | 5 g/L |
| Yeast extract | 5 g/L |
| $KH_2PO_4$ | 1 g/L |
| $MgSO_4.7H_2O$ | 0.2 g/L |
| pH 8 (adjusted with $Na_2CO_3$) | |

A piece of A-581-1 strain (FERM BP-4671) was inoculated into the medium, and cultured at 28° C. for 4 days with shaking. Carotenoids were extracted from the culture and quantitatively analyzed by high performance liquid chromatography according to the same procedure as described in Example 5. A result is shown in Table 9.

TABLE 9

| Astaxanthin mg/L | Adonixanthin mg/L | Total carotenoids mg/L |
|---|---|---|
| 0.17 | 0.64 | 2.81 |

We claim:

1. A process for production of a carotenoid pigment selected from the group consisting of astaxanthin, adonixanthin, β-carotene, echinenone, canthaxanthin, zeaxanthin and mixtures thereof, comprising the steps of:

culturing bacterium strain E-396, FERM BP-4283, or A-581-1, FERM BP-4671, in an aqueous nutrient medium comprising sources of carbon, nitrogen, and inoganic substances and recovering an individual carotenoid pigment or a mixture of the carotenoid pigments.

* * * * *

UNITED STATES PATENT AND TRADEMARK OFFICE
CERTIFICATE OF CORRECTION

PATENT NO.    : 5,607,839
DATED         : March 4, 1997
INVENTOR(S)   : Akira Tsubokura; Hisashi Yoneda;
                Mikihiro Takaki and Takashi Kiyota It is certified that error appears in the above identified patent and that said Letters Patent is hereby corrected as shown below:

On the title page: Item [54] and Column 1, line 1, please amend the title to read as follows:

"PROCESS FOR PRODUCTION OF CAROTENOIDS USING BACTERIA"

Signed and Sealed this

Twenty-second Day of July, 1997

*Attest:*

*Attesting Officer*

BRUCE LEHMAN

*Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1452 base pairs
        ( B ) TYPE: nucleic acid
        ( C ) STRANDEDNESS: double
        ( D ) TOPOLOGY: linear ( i i ) MOLECULE TYPE: cDNA to rRNA ( x i ) SEQUENCE DESCRIPTION: SEQ ID NO:1:

```
AGTTTGATCC  TGGCTCAGAA  CGAACGCTGG  CGGCAGGCTT  AACACATGCA  AGTCGAGCGA      60
```

| | | | | | | |
|---|---|---|---|---|---|---|
| GACCTTCGGG | TCTAGCGGCG | GACGGGTGAG | TAACGCGTGG | GAACGTGCCC | TTCTCTACGG | 120 |
| AATAGCCCCG | GGAAACTGGG | AGTAATACCG | TATACGCCCT | TTGGGGGAAA | GATTTATCGG | 180 |
| AGAAGGATCG | GCCCGCGTTG | GATTAGGTAG | TTGGTGGGGT | AATGGCCCAC | CAAGCCGACG | 240 |
| ATCCATAGCT | GGTTTGAGAG | GATGATCAGC | CACACTGGGA | CTGAGACACG | GCCCAGACTC | 300 |
| CTACGGGAGG | CAGCAGTGGG | GAATCTTAGA | CAATGGGGGC | AACCCTGATC | TAGCCATGCC | 360 |
| GCGTGAGTGA | TGAAGGCCTT | AGGGTTGTAA | AGCTCTTTCA | GCTGGGAAGA | TAATGACGGT | 420 |
| ACCAGCAGAA | GAAGCCCCGG | CTAACTCCGT | GCCAGCAGCC | GCGGTAATAC | GGAGGGGGCT | 480 |
| AGCGTTGTTC | GGAATTACTG | GGCGTAAAGC | GCACGTAGGC | GGACTGGAAA | GTCAGAGGTG | 540 |
| AAATCCCAGG | GCTCAACCTT | GGAACTGCCT | TTGAAACTAT | CAGTCTGGAG | TTCGAGAGAG | 600 |
| GTGAGTGGAA | TTCCGAGTGT | AGAGGTGAAA | TTCGTAGATA | TTCGGAGGAA | CACCAGTGGC | 660 |
| GAAGGCGGCT | CACTGGCTCG | ATACTGACGC | TGAGGTGCGA | AAGCGTGGGG | AGCAAACAGG | 720 |
| ATTAGATACC | CTGGTAGTCC | ACGCCGTAAA | CGATGAATGC | CAGACGTCGG | CAAGCATGCT | 780 |
| TGTCGGTGTC | ACACCTAACG | GATTAAGCAT | TCCGCCTGGG | GAGTACGGTC | GCAAGATTAA | 840 |
| AACTCAAAGG | AATTGACGGG | GGCCCGCACA | AGCGGTGGAG | CATGTGGTTT | AATTCGAAGC | 900 |
| AACGCGCAGA | ACCTTACCAA | CCCTTGACAT | GGCAGGACCG | CTGGAGAGAT | TCAGCTTTCT | 960 |
| CGTAAGAGAC | CTGCACACAG | GTGCTGCATG | GCTGTCGTCA | GCTCGTGTCG | TGAGATGTTC | 1020 |
| GGTTAAGTCC | GGCAACGAGC | GCAACCCACG | TCCCTAGTTG | CCAGCAATTC | AGTTGGGAAC | 1080 |
| TCTATGGAAA | CTGCCGATGA | TAAGTCGGAG | GAAGGTGTGG | ATGACGTCAA | GTCCTCATGG | 1140 |
| GCCTTACGGG | TTGGGCTACA | CACGTGCTAC | AATGGTGGTG | ACAGTGGGTT | AATCCCCAAA | 1200 |
| AGCCATCTCA | GTTCGGATTG | TCCTCTGCAA | CTCGAGGGCA | TGAAGTTGGA | ATCGCTAGTA | 1260 |
| ATCGCGGAAC | AGCATGCCGC | GGTGAATACG | TTCCCGGGCC | TTGTACACAC | CGCCCGTCAC | 1320 |
| ACCATGGGAG | TTGGTTCTAC | CCGACGACGN | TGCGCTAACC | TTCGGGGGGC | AGGCGGCCAC | 1380 |
| GGTAGGATCA | GCGACTGGGG | TGAAGTCGTA | ACAAGGTAGC | CGTAGGGGAA | CCTGCGGCTG | 1440 |
| GATCACCTCC | TT | | | | | 1452 |